United States Patent
Grejda et al.

(10) Patent No.: US 9,557,516 B2
(45) Date of Patent: Jan. 31, 2017

(54) OPTICAL SYSTEMS EXHIBITING IMPROVED LIFETIME USING BEAM SHAPING TECHNIQUES

(71) Applicant: CORNING INCORPORATED, Corning, NY (US)

(72) Inventors: Robert Dennis Grejda, Fairport, NY (US); Keith Ernest Hanford, Macedon, NY (US); Kevin J Magierski, Victor, NY (US); Todd Robert McMichael, Rochester, NY (US)

(73) Assignee: Corning Incorporated, Corning, NY (US)

( * ) Notice: Subject to any disclaimer, the term of this patent is extended or adjusted under 35 U.S.C. 154(b) by 342 days.

(21) Appl. No.: 14/047,200

(22) Filed: Oct. 7, 2013

(65) Prior Publication Data

US 2015/0098131 A1 Apr. 9, 2015

(51) Int. Cl.
G02B 7/02 (2006.01)
G01N 21/95 (2006.01)
G03F 7/20 (2006.01)
G02B 5/18 (2006.01)

(52) U.S. Cl.
CPC ............ *G02B 7/025* (2013.01); *G01N 21/9501* (2013.01); *G03F 7/70825* (2013.01); *G01N 2201/061* (2013.01)

(58) Field of Classification Search
CPC G03F 7/7015; G03F 7/70141; G03F 7/70283; G03F 7/70825; G03F 7/70916; G03F 7/70933; H01L 29/06; H01S 5/005; H01S 5/4012; H01S 5/4025

USPC ........ 359/558, 566, 811, 819, 822; 257/622; 29/429

See application file for complete search history.

(56) References Cited

U.S. PATENT DOCUMENTS

| | | | |
|---|---|---|---|
| 5,493,442 A | 2/1996 | Buchholz et al. |
| 6,229,657 B1 | 5/2001 | Holderer et al. |
| 6,285,496 B1 | 9/2001 | Bauer et al. |
| 6,552,862 B2 | 4/2003 | Dieker |
| 7,081,278 B2 | 7/2006 | Lipson et al. |
| 7,154,682 B2 | 12/2006 | Umezu et al. |
| 7,232,595 B2 | 6/2007 | Coykendall et al. |

(Continued)

OTHER PUBLICATIONS

International Search Report and Written Opinion, dated Feb. 13, 2015, International Application No. PCT/US2014/058766, International Filing Date Oct. 2, 2014 pp. 1-13.

*Primary Examiner* — Bumsuk Won
*Assistant Examiner* — Collin X Beatty
(74) *Attorney, Agent, or Firm* — Kevin L. Bray (57) ABSTRACT

An optical system includes a lens assembly and a light source. The lens assembly includes an optical lens positioned to transmit and refract light provided by the light source, and a lens holder coupled to the optical lens and maintaining a position of the optical lens relative to the light source. The optical lens is coupled to the lens holder with a bonding agent arranged in an interrupted configuration at positions proximate to a circumference of the optical lens. The light source provides light to the optical lens of the lens assembly that has an optical footprint that includes a plurality of high-intensity regions separated from one another by low-intensity regions and the bonding agent is positioned in a circumferential orientation relative to the light source such that the bonding agent is spaced apart from the high-intensity regions of the optical footprint of the light.

13 Claims, 7 Drawing Sheets

(56) References Cited

U.S. PATENT DOCUMENTS

| | | |
|---|---|---|
| 7,256,221 B2 | 8/2007 | Coykendall et al. |
| 2006/0061886 A1* | 3/2006 | Gellrich .............. G03F 7/70933 |
| | | 359/811 |
| 2006/0114440 A1* | 6/2006 | Sekigawa ............. G03F 7/2057 |
| | | 355/69 |
| 2011/0128639 A1* | 6/2011 | Honda ................... G02B 7/025 |
| | | 359/819 |
| 2011/0205643 A1* | 8/2011 | Schreiber ............ C23C 14/0694 |
| | | 359/819 |
| 2012/0050894 A1* | 3/2012 | Honma .................. G02B 7/023 |
| | | 359/819 |
| 2013/0256844 A1* | 10/2013 | Talor ........................ G03F 1/30 |
| | | 257/622 |

* cited by examiner

OPTICAL SYSTEMS EXHIBITING IMPROVED LIFETIME USING BEAM SHAPING TECHNIQUES

TECHNICAL FIELD

The present specification generally relates to lens assemblies for positioning an optical lens relative to a light source.

BACKGROUND

Lens systems are used in a variety of end-user applications, including in lithography and semiconductor inspection equipment. In these applications, light from a light source is introduced to the lens elements to perform the manufacturing operation. However, in some applications, the light introduced to the lens elements may tend to degrade a bonding agent that is positioned to couple the lens element to a lens holder. Degradation of the bonding agent may lead to contamination of the equipment and/or misalignment of the lens element relative to the light source.

Accordingly, alternative lens assemblies may be desired.

SUMMARY

In one embodiment, an optical system includes a lens assembly and a light source. The lens assembly includes an optical lens positioned to transmit and refract light provided by the light source, and a lens holder coupled to the optical lens and maintaining a position of the optical lens relative to the light source. The optical lens is coupled to the lens holder with a bonding agent arranged in an interrupted configuration at positions proximate to a circumference of the optical lens. The light source provides light to the optical lens of the lens assembly. The light provided to the optical lens has an optical footprint that includes a plurality of high-intensity regions separated from one another by low-intensity regions and the bonding agent is positioned in a circumferential orientation relative to the light source such that the bonding agent is spaced apart from the high-intensity regions of the optical footprint of the light.

In another embodiment, a lens assembly includes an optical lens, a lens holder having a fastening portion and a lens support portion coupled to the fastening portion, and a bonding agent. The lens support portion includes a plurality of support pads that are spaced apart from relief channels. The bonding agent is positioned between at least a portion of the plurality of support pads and the optical lens, so that the bonding agent secures the optical lens to the lens holder.

Additional features and advantages of the embodiments described herein will be set forth in the detailed description which follows, and in part will be readily apparent to those skilled in the art from that description or recognized by practicing the embodiments described herein, including the detailed description that follows, the claims, as well as the appended drawings.

It should be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Reference will now be made in detail to embodiments of lens assembly having optical lenses and lens holders and optical systems that incorporate lens assemblies having optical lenses and lens holders. One embodiment of an optical system incorporating a lens assembly having an optical lens and a lens holder. The optical lens is secured to the lens holder by a bonding agent. The bonding agent is arranged in an interrupted configuration at positions proximate to a circumference of the optical lens. The lens assembly including the optical lens and the lens holder may be incorporated into an optical system, along with a light source that provides light to the optical lens. The light provided by the light source has an optical footprint that includes a plurality of high-intensity regions and a plurality of low-intensity regions. The lens assembly is positioned in a circumferential orientation such that the bonding agent is spaced apart from the high-intensity regions of the optical footprint of the light. These and other embodiments will be described in more detail with reference to the appended figures.

Figure 1:
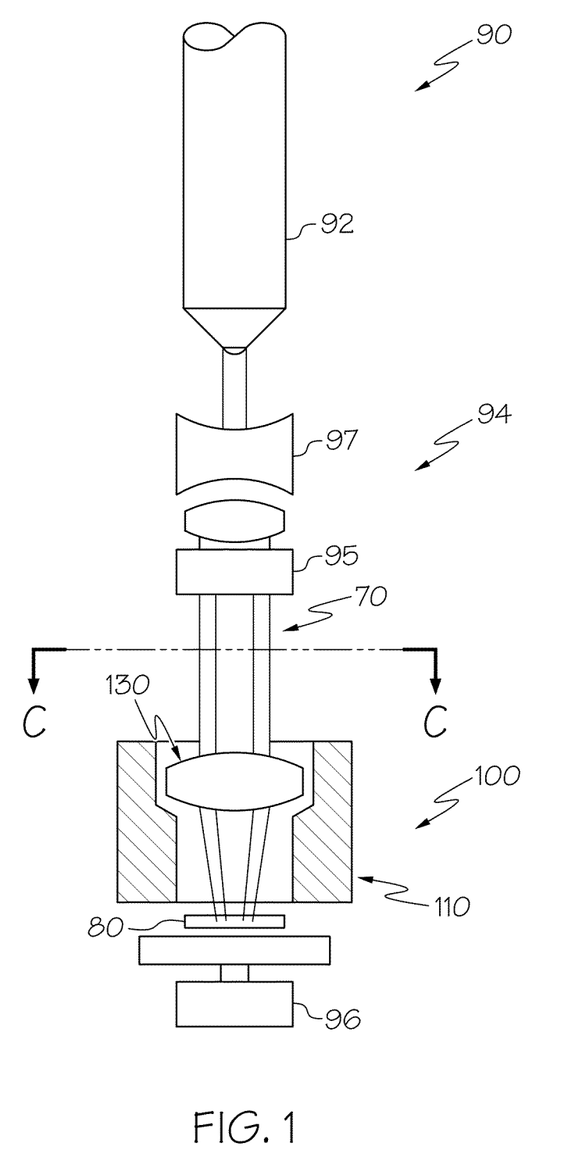
FIG. 1 schematically depicts a cut-away front view of an optical system having an optical lens coupled to a lens holder according to one or more embodiments shown or described herein.

Referring to FIG. 1 in detail, a portion of an optical system 90 is schematically depicted with certain components cut-away for clarity. In the depicted embodiment, the optical system 90 includes a light source 92, at least one beam shaping element 94, a lens assembly 100, and a part carrier 96. The lens assembly 100 includes a lens holder 110 and an optical lens 130. Light provided by the light source 92 is directed through the optical lens 130 of the lens assembly 100, which transmits and refracts the light towards a workpiece 80 that is supported on the part carrier 96. The optical system 90 may be used to perform a manufacturing operation on the workpiece 80, for example, inspecting the workpiece 80 or modifying the workpiece 80, for example in a lithography process.

In the depicted embodiment, the light introduced to the lens assembly 100 has an optical footprint 70 that corresponds to the manufacturing operation that the optical system 90 is performing. In the depicted embodiment, the light source 92 provides a generally uniform beam of light that is modified by the at least one beam shaping element 94 before the light enters the lens assembly 100. In one embodiment, the at least one beam shaping element 94 may be a reticle 95 that is positioned between the optical lens 130 and the light source 92. In other embodiments, the at least one beam shaping element 94 may be an apodizer or a diffraction grating. The reticle 95 may have a plurality of masked regions and unmasked regions through which the light from the light source 92 is directed. After passing through the reticle 95, the light from the light source 92 includes a plurality of high-intensity regions, which correspond to the unmasked regions of the reticle 95, and a plurality of low-intensity regions, which correspond to the masked regions of the reticle 95. In other embodiments, the at least one beam shaping element 94 includes a diffractive optical element 97 positioned between the light source 92 and the optical lens 130. In these embodiments, the diffractive optical element 97 may transmit and refract light that is cast from the light source 92 so that the beam of light that exits the diffractive optical element 97 includes a plurality of high-intensity regions and a plurality of low-intensity regions separating the high-intensity regions from one another.

In yet other embodiments, the light source 92 may provide light having a plurality of high-intensity regions and a plurality of low-intensity regions separating the high-intensity regions from one another.

Figure 2:
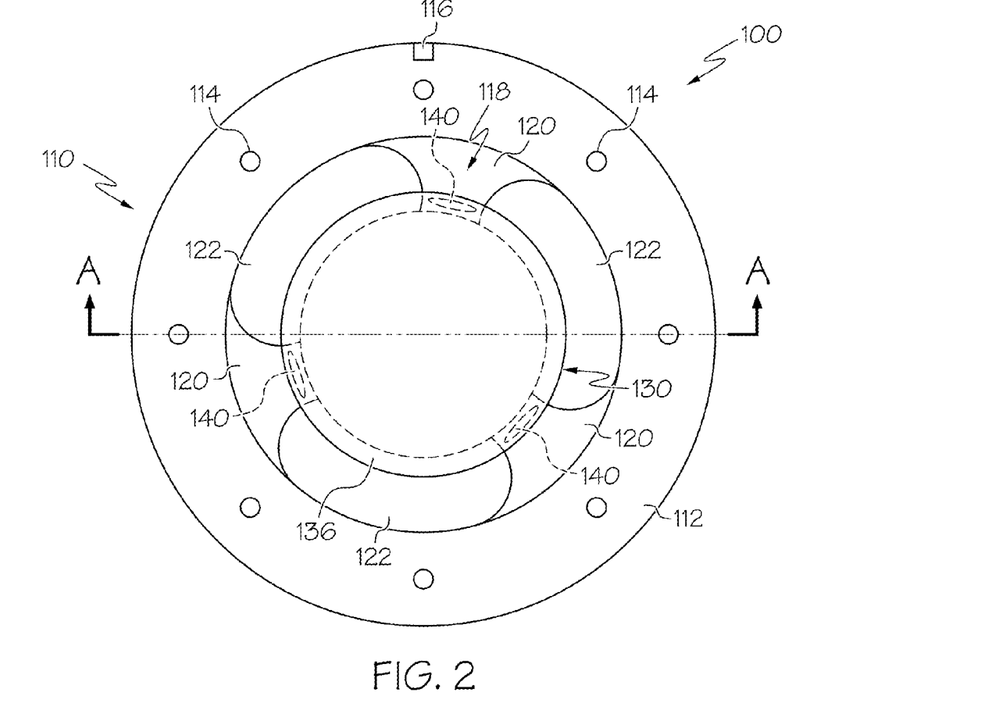
FIG. 2 schematically depicts a top view of a lens assembly having an optical lens coupled to a lens holder according to one or more embodiments shown or described herein.

Referring now to FIG. 2, one embodiment of the lens assembly 100 is depicted. In this embodiment, the lens assembly 100 includes a lens holder 110 and an optical lens 130. The lens holder 110, shown in cross-section in FIG. 3, includes a fastening portion 112 and a lens support portion 118. The fastening portion 112 includes a plurality of mounting elements 114, here through holes that pass through the fastening portion 112, that provide securement locations to couple the lens holder 110 in the optical system and/or to other lens holders within the optical system. The fastening portion 112 may also include a clocking element 116, for example, a key and/or keyway. The clocking element 116 may provide an orientation reference between adjacent components of the optical system 90 so that alignment of the components of the optical system 90 can be maintained.

Figure 4:
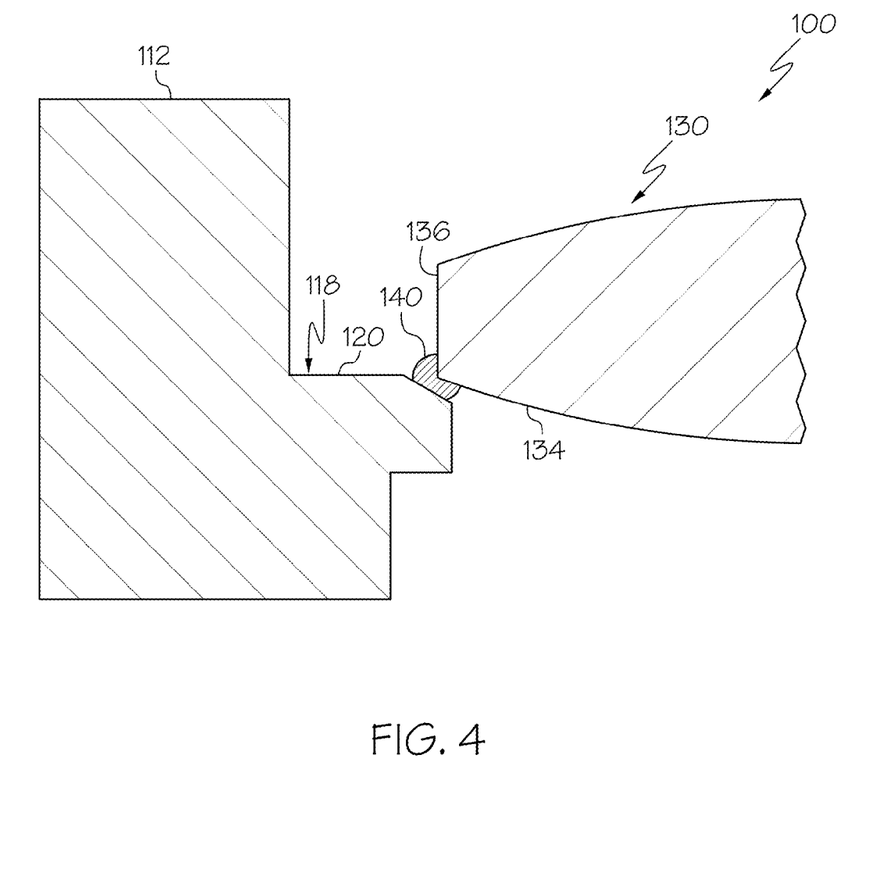
FIG. 4 schematically depicts a detailed sectional front view of a lens assembly having an optical lens coupled to a lens holder shown at view J of FIG. 3 according to one or more embodiments shown or described herein.

In the depicted embodiment, the lens support portion 118 extends in a radially inward orientation from the fastening portion 112. The lens support portion 118 may include a planar portion 124 and a contoured portion 126, as depicted in detail in FIG. 4. In this embodiment, the contoured portion 126 is located at radially inward positions from the planar portion 124. The contoured portion 126 may be shaped to conform to the general shape of the optical lens 130 at positions at which the optical lens 130 is coupled to the lens support portion 118 by the bonding agent 140.

Referring again to FIGS. 2 and 3, an attachment portion 134 of the optical lens 130 is coupled to the lens support portion 118 with a bonding agent 140. The bonding agent 140 is positioned at a plurality of positions arranged in a circumferential orientation around the optical lens 130. Regions of the bonding agent 140 are separated from one another at intermediate circumferential positions between the regions of the bonding agent 140, so that the lens assembly 100 is generally free of bonding agent 140 at circumferential positions between the regions of the bonding agent 140.

Suitable materials for the bonding agent 140 include materials that are commercially available, including cements and adhesives, examples of which are discussed in U.S. Pat. Nos. 7,232,595 and 7,256,221, which are hereby incorporated by reference in their entirety. When assembling the lens assembly 100, the bonding agent 140 may be positioned in the desired locations along the lens support portion 118 of the lens holder 110. The optical lens 130 may be inserted and held in position relative to datum features of the lens holder 110, including the clocking element 116. The optical lens 130 may be held in position until the bonding agent 140 has an opportunity to dry or cure, thereby maintaining the position of the optical lens 130 relative to the datum features of the lens holder 110. These materials typically satisfy operational requirements of elastic modulus and coefficient of thermal expansion, and are well suited for use in optical systems 90 described herein.

The materials conventionally used as the bonding agent 140, however, may be prone to degradation when illuminated by particular light sources. The degradation may be particularly acute when the light source emits light at short wavelengths, for example at wavelengths corresponding to deep ultra-violet and extreme ultra-violet wavelengths. At short wavelengths, energy from the light source has a tendency to break down the materials of the bonding agent 140. The degradation of the material may cause outgassing of the bonding agent 140, which may lead to contamination of the optical system 90. Degradation of the bonding agent 140 may also negatively affect the tensile strength and/or the elasticity of the bonding agent 140, which may reduce the ability of the bonding agent 140 to maintain the position of the optical lens 130 relative to the datum features of the lens holder 110. Misalignment between the optical lens 130 and the datum features of the lens holder 110 may reduce the performance characteristics of the optical system 90.

Figure 3:
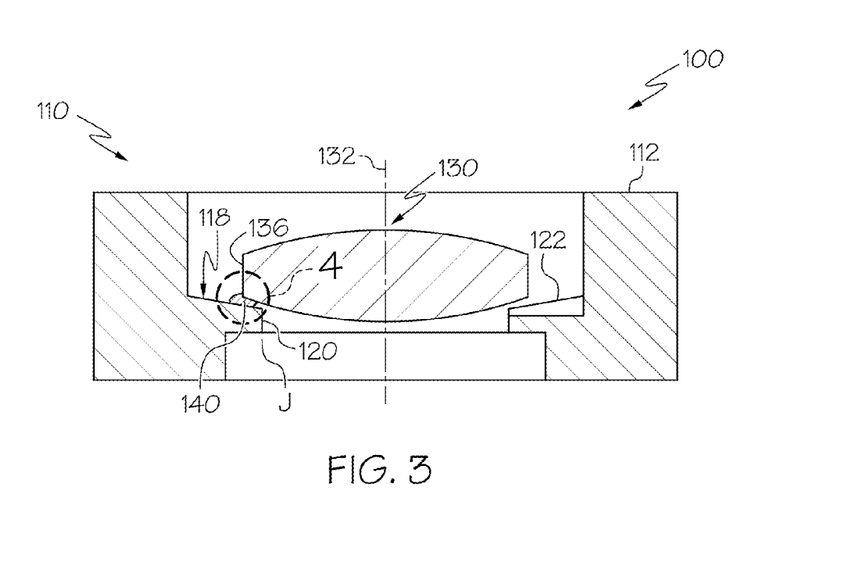
FIG. 3 schematically depicts a sectional front view of a lens assembly having an optical lens coupled to a lens holder shown along line A-A of FIG. 2 according to one or more embodiments shown or described herein.

In the embodiment depicted in FIGS. 2 and 3, the lens support portion 118 includes a plurality of support pads 120 that are arranged at circumferential orientations around the lens support portion 118. The plurality of support pads 120 are each separated from one another by relief channels 122 that are spaced apart from the support pads 120 in a direction corresponding to an optical axis 132 of the optical lens 130. The support pads 120 and the relief channels 122 provide an interrupted mounting plane along the lens support portion 118 to which the optical lens 130 is coupled. In this embodiment, bonding agent 140 is positioned along the support pads 120 to contact the optical lens 130. The bonding agent 140 is generally not positioned at positions proximate to the relief channels 122, such that the optical lens 130 is separated from the lens holder 110 at positions proximate to the relief channels 122. The spacing between the optical lens 130 and the relief channels 122 of the lens holder 110 provides a gap through which fluid may travel. In certain embodiments of the optical system 90, purge gas may be introduced to the lens assembly 100 and flow through the gap created between the relief channels 122 and the optical lens 130 to flush any contaminants.

While the embodiment of FIGS. 2 and 3 depicts a lens holder 110 that incorporates three support pads 120, and therefore three relief channels 122 and three regions of bonding agent 140, it should be understood that the lens holder 110 may include any number of support pads 120, relief channels 122, and regions of bonding agent 140 as dictated by the design and requirements of the optical system 90.

Figure 5:
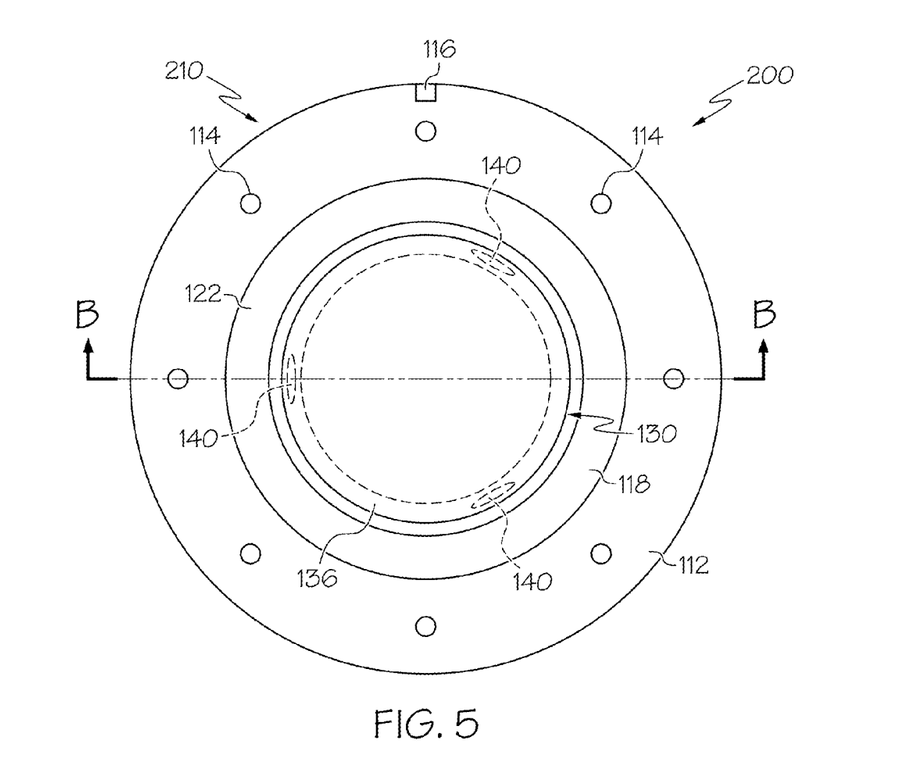
FIG. 5 schematically depicts a top view of a lens assembly having an optical lens coupled to a lens holder according to one or more embodiments shown or described herein.
Figure 6:
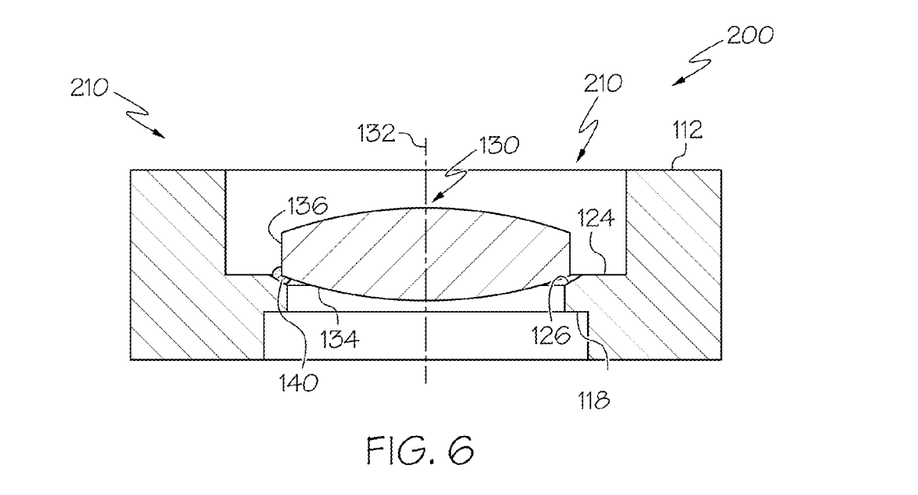
FIG. 6 schematically depicts a sectional front view of a lens assembly having an optical lens coupled to a lens holder shown along line B-B of FIG. 5 according to one or more embodiments shown or described herein.

Referring now to FIGS. 5 and 6, another embodiment of the lens assembly 200 incorporating a lens holder 210 and the optical lens 130 is depicted. In this embodiment, the lens holder 210 includes a fastening portion 112 and a lens support portion 118. The fastening portion 112 includes a plurality of mounting elements 114, here through holes that pass through the fastening portion 112, that provide securement locations to couple the lens holder 210 in the optical system. The fastening portion 112 may also include a clocking element 116, for example, a key and/or keyway. The clocking element 116 may provide an orientation reference between adjacent components of the optical system 90 so that radial alignment of the components of the optical system 90 can be maintained.

In this embodiment, the lens support portion 118 may be continuous in shape around its circumference 136, such that the lens support portion 118 is uninterrupted in the circumferential orientation. The optical lens 130 is coupled to the lens support portion 118 with bonding agent 140 positioned in discrete regions that are arranged at positions proximate to the circumference 136 of the optical lens 130. The bonding agent 140 may generally be limited to be positioned within the discrete regions only, so that bonding agent 140 is not located at positions between adjacent regions.

Because the bonding agent 140 is positioned in discrete regions between the lens support portion 118 of the lens holder 110 and the optical lens 130, and because the bonding agent 140 may have a thickness, the optical lens 130 may be positioned above the lens support portion 118 by the bonding agent 140. In these embodiments, at positions between the discrete regions of bonding agent 140, the spacing between the lens support portion 118 and the optical lens 130 may provides a gap through which fluid may travel. In certain embodiments of the optical system 90, purge gas may be introduced to the lens assembly 200 and flow through the gap created between the lens support portion 118 and the optical lens 130 at positions spaced apart from the discrete regions of bonding agent 140 to flush any contaminants.

Figure 7:
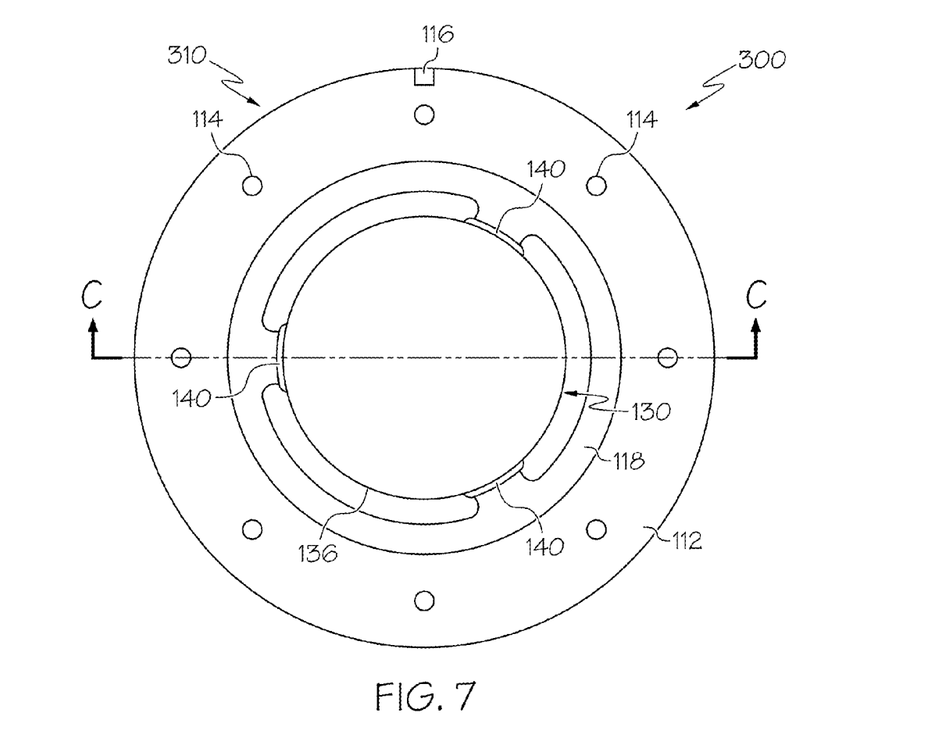
FIG. 7 schematically depicts a top view of a lens assembly having an optical lens coupled to a lens holder according to one or more embodiments shown or described herein.
Figure 8:
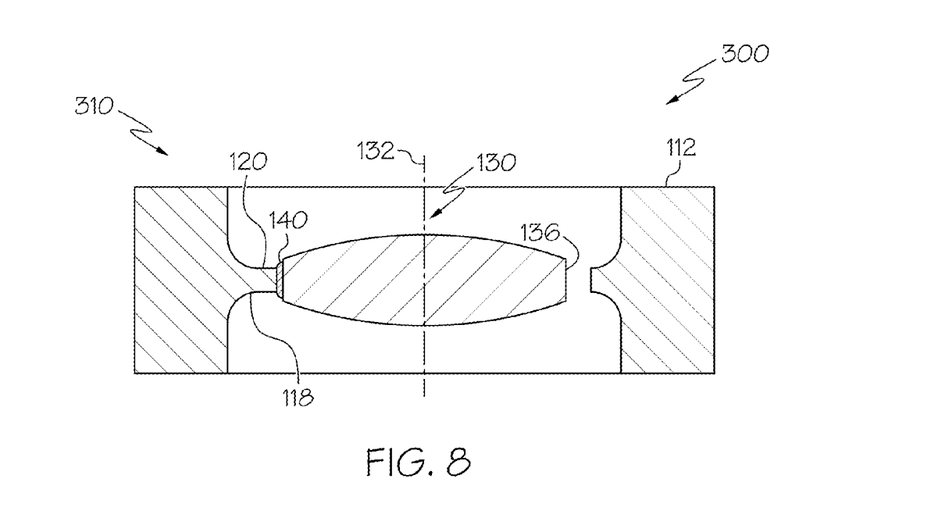
FIG. 8 schematically depicts a sectional front view of a lens assembly having an optical lens coupled to a lens holder shown along line C-C of FIG. 7 according to one or more embodiments shown or described herein.

Referring now to FIGS. 7 and 8, another embodiment of the lens assembly 300 incorporating a lens holder 310 and the optical lens 130 is depicted. In this embodiment, the lens holder 310 includes a fastening portion 112 and a lens support portion 118. The fastening portion 112 includes a plurality of mounting elements 114, here through holes that pass through the fastening portion 112, that provide attachment locations to couple the lens holder 310 in the optical system. The fastening portion 112 may also include a clocking element 116, for example, a key and/or keyway. The clocking element 116 may provide an orientation reference between adjacent components of the optical system 90 so that radial alignment of the components of the optical system 90 can be maintained.

In this embodiment, the optical lens 130 is coupled to the lens holder 310 with a plurality of discrete regions of bonding agent 140 that are arranged around the circumference 136 of the optical lens 130. The discrete regions of bonding agent 140 are positioned to contact the optical lens 130 and the lens holder 310 in a circumferential orientation corresponding to a radial direction of the optical lens 130 transverse to the optical axis 132 of the optical lens 130. Embodiments of the lens holder 310 may include support pads 322 that extend from relief channels 324 in a generally radial direction. However, embodiments of the lens holder 310 may alternatively include an uninterrupted interface diameter. Discrete regions of bonding agent 140 may be positioned around the circumference 136 of the optical lens 130 between the optical lens 130 and the lens holder 310 to couple the optical lens to the lens holder 310. In the depicted embodiment, the discrete regions of bonding agent 140 may be positioned proximate to the support pads 322 of the lens holder 310 and spaced apart from the relief channels 324 of the lens holder 310.

Because the bonding agent 140 is positioned in discrete regions between the lens support portion 118 of the lens holder 310 and the optical lens 130, and because the bonding agent 140 may have a thickness, the optical lens 130 may be positioned radially inward from the lens support portion 118 by the bonding agent 140. In these embodiments, at positions between the discrete regions of bonding agent 140, the spacing between the lens support portion 118 and the optical lens 130 provides a gap through which fluid may travel. In certain embodiments of the optical system 90, purge gas may be introduced to the lens assembly 300 and flow through the gap created between the lens support portion 118 and the optical lens 130 at positions spaced apart from the discrete regions of bonding agent 140 to flush any contaminants.

In the embodiments of the lens assembly 100, 200, 300 described hereinabove, by limiting the positions at which the bonding agent 140 is located to certain discrete regions arranged at positions proximate to the circumference 136 of the optical lens 130, the bonding agent 140 may be selectively positioned so that the bonding agent 140 is spaced apart from high-intensity regions of the light that is directed through the lens assembly 100, 200, 300. By maintaining spacing between the high-intensity regions of the light pattern and the bonding agent 140, degradation of the bonding agent 140 due to light input to the lens assembly 100, 200, 300 may be minimized.

Referring now to FIGS. 9-12, portions of the optical system 90 having a lens assembly 100 according to embodiments of the present disclosure are depicted. In these embodiments, the light source (not shown) provides light to the optical lens 130 of the lens assembly 100 having an optical footprint 70 that includes a plurality of high-intensity regions 72 that are separated from one another by a plurality of low-intensity regions 74. In the embodiment depicted in FIG. 9, the high-intensity regions 72 are arranged to pass through the center portion of the optical lens 130, and are separated from one another at positions around the circumference 136 of the optical lens 130. As discussed hereinabove, the light provided by the light source may be modified through a variety of light-shaping devices so that the light introduced to the optical lens 130 has the designated optical footprint 70.

Figure 10:
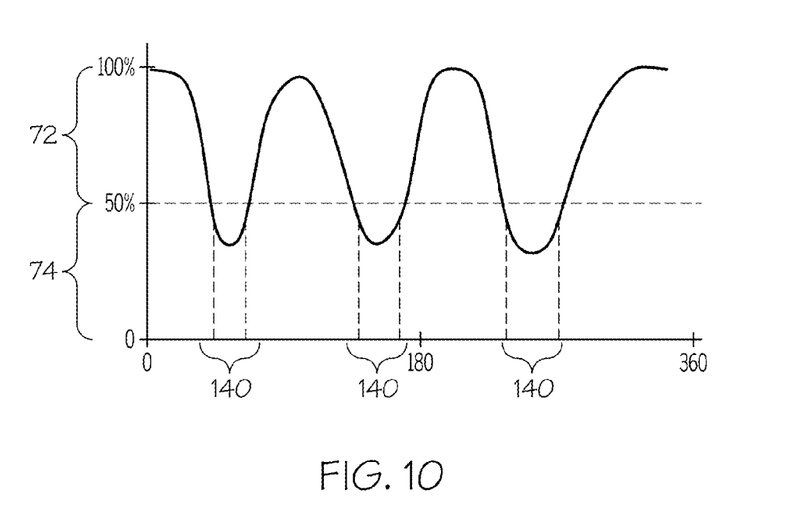
FIG. 10 schematically depicts a hypothetical plot of intensity of the light of FIG. 9 evaluated around the circumference of the optical lens.

Referring now to FIG. 10, a hypothetical plot of beam intensity evaluated around the circumference 136 of the optical lens 130 is depicted. As illustrated in the hypothetical plot, the optical footprint 70 of the light varies at positions around the circumference 136, where the intensity of the light is greater in positions corresponding to the high-intensity regions 72 than in positions corresponding to the low-intensity regions 74. In some embodiments, the intensity of the light at positions corresponding to the low-intensity regions 74 of the optical footprint 70 may be less than about 50% of the maximum intensity of the light evaluated in the high-intensity regions 72 of the optical footprint 70. In other embodiments, the intensity of the light at positions corresponding to the low-intensity regions 74 of the optical footprint 70 may be less than about 25% of the maximum intensity of the light evaluated in the high-intensity regions 72 of the optical footprint 70. In yet other embodiments, the intensity of the light at positions corresponding to the low-intensity regions 74 of the optical footprint 70 may be less than about 10% of the maximum intensity of the light evaluated in the high-intensity regions 72 of the optical footprint 70. In yet other embodiments, the intensity of the light at positions corresponding to the low-intensity regions 74 of the optical footprint 70 may be less than the median intensity of the light evaluated along the circumference of the optical lens and the high-intensity regions 72 of the optical footprint 70 may be greater than the median intensity of light evaluated along the circumference of the optical lens. While the intensity of the light depicted in the hypothetical plot of FIG. 10 shows smooth transitions between the high-intensity regions 72 and the low-intensity regions 74, it should be understood that the intensity of the light may transition from the high-intensity regions 72 to the low-intensity regions 74 over short distances evaluated around the circumference 136 of the optical lens 130 so that the intensity of the optical footprint 70 resembles a step function.

Bonding agent 140 may be positioned along the lens holder 110 at positions corresponding to the low-intensity regions 74 of the optical footprint 70. Because of the reduce intensity of the light at positions corresponding to the low-intensity regions 74 as compared with the high-intensity regions 72 of the optical footprint 70, the light that is directed onto the bonding agent 140 at positions corresponding to the low-intensity regions 74 may not degrade the bonding agent 140 and/or may reduce the rate of degradation of the bonding agent 140. Accordingly, by positioning the bonding agent 140 at circumferential regions around the lens holder 110 at which the light has a low intensity, reduction in coupling performance and/or outgassing of the bonding agent 140 may be improved as compared to positioning the bonding agent 140 in positions which the bonding agent 140 would be subject to high-intensity light. By selectively restricting the bonding agent 140 to be positioned in low-intensity regions 74 of the optical footprint 70, the bonding agent 140 may have improved life expectancy and lower likelihood of contamination as compared to designs that position the bonding agent 140 in the high-intensity regions 72 of the optical footprint 70.

Figure 11:
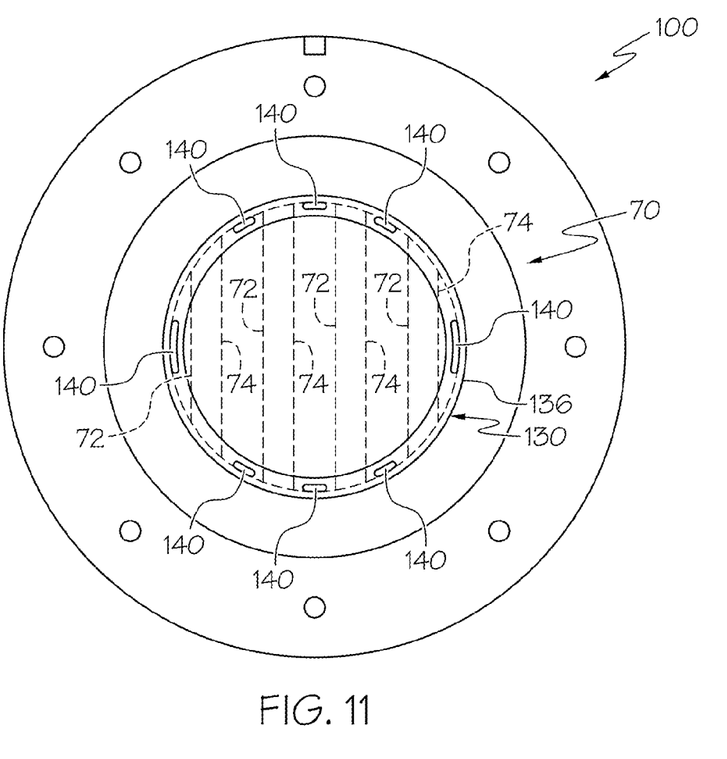
FIG. 11 schematically depicts a top view of a lens assembly having an optical lens coupled to a lens holder and a light having an optical footprint cast onto the optical lens according to one or more embodiments shown or described herein.

Referring now to FIG. 11, another embodiment of the lens assembly 100 is depicted. In this embodiment, the light source (not shown) provides light to the optical lens 130 of the lens assembly 100 having an optical footprint 170 that includes a plurality of high-intensity regions 72 that are separated from one another by a plurality of low-intensity regions 74. In the embodiment depicted in FIG. 11, the high-intensity regions 72 are arranged in a "striped" orientation so that the high-intensity regions 72 and the low-intensity regions 74 alternate with one another when evaluated along a cross-wise direction of the optical lens 130.

Figure 12:
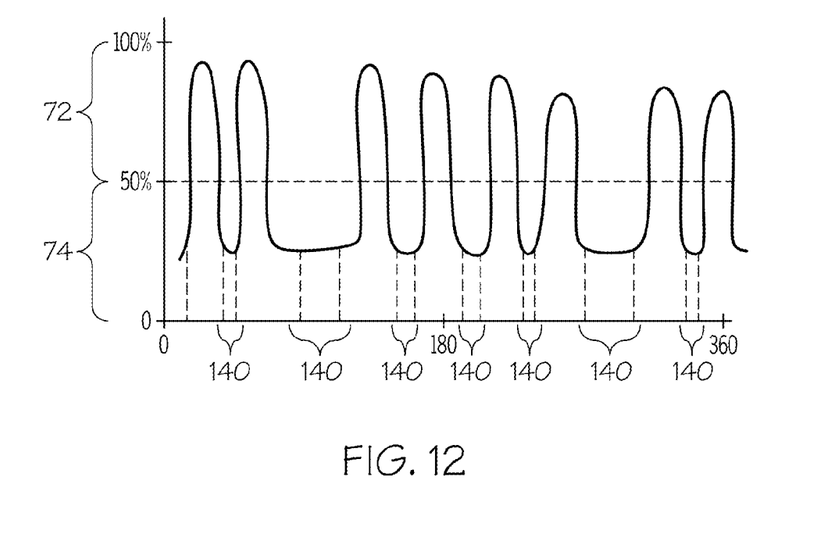
FIG. 12 schematically depicts a hypothetical plot of intensity of the light of FIG. 11 evaluated around the circumference of the optical lens.

Referring now to FIG. 12, a hypothetical plot of beam intensity evaluated around the circumference 136 of the optical lens 130 is depicted. As illustrated in the hypothetical plot, the optical footprint 170 of the light varies at positions around the circumference 136, where the intensity of the light is greater in positions corresponding to the high-intensity regions 72 than in positions corresponding to the low-intensity regions 74. In some embodiments, the intensity of the light at positions corresponding to the low-intensity regions 74 of the optical footprint 170 may be less than about 50% of the maximum intensity of the light evaluated in the high-intensity regions 72 of the optical footprint 170. In other embodiments, the intensity of the light at positions corresponding to the low-intensity regions 74 of the optical footprint 170 may be less than about 25% of the maximum intensity of the light evaluated in the high-intensity regions 72 of the optical footprint 170. In yet other embodiments, the intensity of the light at positions corresponding to the low-intensity regions 74 of the optical footprint 170 may be less than about 10% of the maximum intensity of the light evaluated in the high-intensity regions 72 of the optical footprint 170. While the intensity of the light depicted in the hypothetical plot of FIG. 12 shows smooth transitions between the high-intensity regions 72 and the low-intensity regions 74, it should be understood that the intensity of the light may transition from the high-intensity regions 72 to the low-intensity regions 74 over short distances evaluated around the circumference 136 of the optical lens 130 so that the intensity of the optical footprint 170 resembles a step function.

Figure 9:
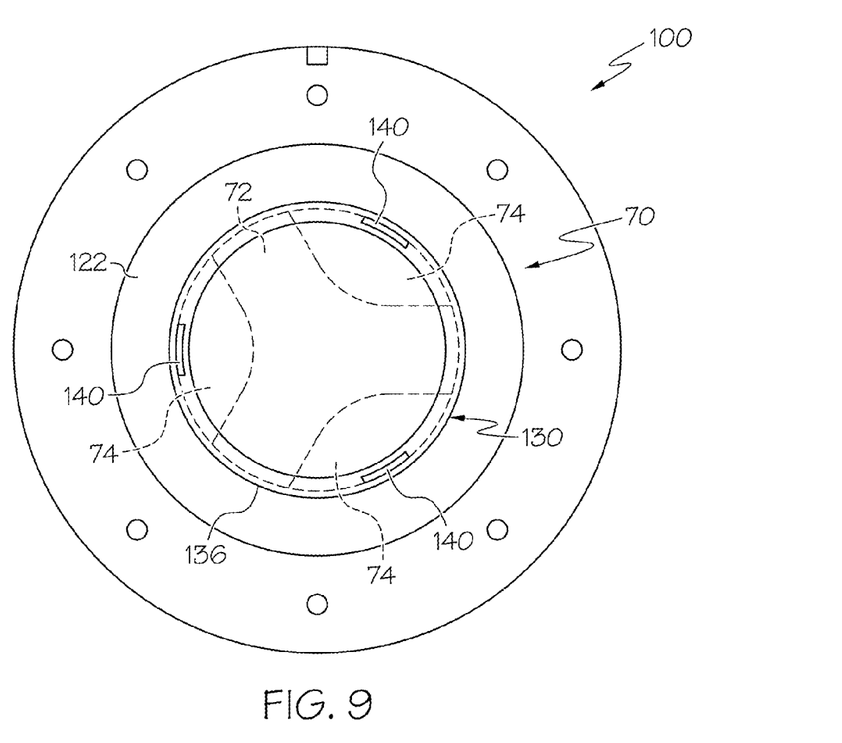
FIG. 9 schematically depicts a top view of a lens assembly having an optical lens coupled to a lens holder and a light having an optical footprint cast onto the optical lens according to one or more embodiments shown or described herein.

Similar to the embodiment discussed with respect to FIGS. 9 and 10 hereinabove, bonding agent 140 may be positioned along the lens holder 110 at positions corresponding to the low-intensity regions 74 of the optical footprint 170. Because of the reduce intensity of the light at positions corresponding to the low-intensity regions 74 as compared with the high-intensity regions 72 of the optical footprint 170, the light that is directed onto the bonding agent 140 at positions corresponding to the low-intensity regions 74 may not degrade the bonding agent 140 and/or may reduce the rate of degradation of the bonding agent 140. Accordingly, by positioning the bonding agent 140 at circumferential regions around the lens holder 110 at which the light has a low intensity, reduction in coupling performance and/or outgassing of the bonding agent 140 may be improved as compared to positioning the bonding agent 140 in positions which the bonding agent 140 would be subject to high-intensity light. By selectively restricting the bonding agent 140 to be positioned in low-intensity regions 74 of the optical footprint 170, the bonding agent 140 may have improved life expectancy and lower likelihood of contamination as compared to designs that position the bonding agent 140 in the high-intensity regions 72 of the optical footprint 170.

While particular embodiments of the optical footprints 70, 170 are depicted in FIGS. 9-12, it should be understood that a variety of configurations of the optical footprints may be introduced to the optical system 90 by various light-shaping devices without departing from the scope of the present disclosure. The particular optical footprint may be suited to the manufacturing operation in which the optical system 90 is designed for use.

It should now be understood that lens assemblies and optical systems that include lens assemblies according to the present disclosure include a lens holder and an optical lens. The optical lens is coupled to the lens holder with a bonding agent that is interrupted at positions proximate to the circumference of the optical lens. Light in the optical system is provided in an optical footprint that has a plurality of high-intensity regions that are separated from a plurality of low-intensity regions evaluated along the circumference of the optical lens. The lens assembly is positioned in the optical system so that the bonding agent is spaced apart from the high-intensity regions of the optical footprint.

It is noted that the term "substantially" may be utilized herein to represent the inherent degree of uncertainty that may be attributed to any quantitative comparison, value, measurement, or other representation. This term is also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

The invention claimed is:

1. An optical system comprising:
a light source and a lens assembly, the lens assembly, comprising:
an optical lens positioned to transmit and refract light provided by the light source; and
a lens holder coupled to the optical lens and maintaining a position of the optical lens relative to the light source, the optical lens coupled to the lens holder with a bonding agent arranged in an interrupted configuration at positions proximate to a circumference of the optical lens such that the lens assembly comprises a gap between the lens holder and the optical lens,
wherein the light source provides light to the optical lens of the lens assembly,
wherein the light provided to the optical lens has an optical footprint that includes a plurality of high-intensity regions separated from one another by low-intensity regions;
wherein the intensity of the light evaluated around the circumference of the optical lens approximates a step function;
wherein the intensity of the light in the low-intensity regions of the step function is less than about 50% of the maximum intensity of the light in the high-intensity regions of the step function; and
wherein the bonding agent is positioned in a circumferential orientation relative to the light source such that the bonding agent is spaced apart from the high-intensity regions of the optical footprint of the light.

2. The optical system of claim 1, wherein the high-intensity regions include a portion of the optical footprint that has an intensity greater than or equal to a median intensity of the light across the optical footprint.

3. The optical system of claim 1, further comprising a beam shaping element coupled to the optical system to provide the optical footprint in the light provided to the optical lens.

4. The optical system of claim 3, wherein the beam shaping element comprises a reticle positioned between the optical lens and the light source, the reticle having a plurality of masked regions and unmasked regions, wherein the high-intensity regions of the optical footprint generally correspond to the unmasked regions of the reticle and the low-intensity regions of the optical footprint generally correspond to the masked regions of the reticle.

5. The optical system of claim 3, wherein the beam shaping element comprises a diffractive optical element positioned between the optical lens and the light source.

6. The optical system of claim 1, wherein the light source comprises a laser diode array that provides the light to the optical lens having the optical footprint.

7. The optical system of claim 1, wherein the lens holder comprises a planar portion and a contoured portion abutting the planar portion and the bonding agent is positioned to contact the contoured portion and a portion of the optical lens at predefined locations at positions proximate to the circumference of the optical lens.

8. The optical system of claim 7, wherein the lens holder further comprises a plurality of support pads that are spaced apart from relief channels and the bonding agent is positioned proximate to the support pads.

9. The optical system of claim 8, wherein the plurality of support pads are spaced apart from the relief channels in a direction of an optical axis of the optical lens.

10. The optical system of claim 8, wherein the plurality of support pads are spaced apart from the relief channels in a radial direction relative to an optical axis of the optical lens.

11. The optical system of claim 1, wherein the lens holder further comprises a clocking element positioned at a predefined circumferential orientation relative to the light source.

12. The optical system of claim 1, wherein the intensity of the light in the low-intensity regions is less than about 25% of the maximum intensity of the light in the high-intensity regions.

13. The optical system of claim 1, wherein the intensity of the light in the low-intensity regions is less than about 10% of the maximum intensity of the light in the high-intensity regions.

* * * * *